United States Patent [19]

Bachynsky

[11] Patent Number: 4,555,397
[45] Date of Patent: Nov. 26, 1985

[54] METHOD FOR ANTI-CHOLINERGIC BLOCKAGE OF WITHDRAWAL SYMPTOMS IN SMOKING CESSATION

[76] Inventor: Nicholas Bachynsky, 7322 SW. Freeway, Houston, Tex. 77074

[21] Appl. No.: 522,858

[22] Filed: Aug. 12, 1983

[51] Int. Cl.[4] .................... A61K 31/24; A61K 31/44; A61K 31/54
[52] U.S. Cl. .................................. 424/10; 514/223; 514/304; 514/557
[58] Field of Search ........................ 424/10, 246, 265; 546/91, 131; 514/223, 304, 557

[56] References Cited

U.S. PATENT DOCUMENTS 3,764,680 10/1973 Phillips ............................. 424/272

OTHER PUBLICATIONS

Physician's Desk Reference, pp. 1915–1918 (1983).
Goodman and Gilman's The Pharmacological Basis of Therapeutics, 6th Ed., pp. 394–414.
Brimblecombe, R. W., Drug Actions on Cholinergic Systems, University Park Press (1974), pp. 93–97.
Ketchum, J. S. et al., Atropine, Scopolamine and Ditran: Comparative Pharmacology and Antagonists in Man, Psychopharmacologia, 28, pp. 121–145 (1974).
Gordon, "Psychopharmacological Agents", vol. II, Academic Press, New York, 1967, pp. 38–39.
Ebenezer, "Atropine Pretreatment Reverses the Initial Depressant Effect of Nicotine on the Spontaneous Activity of Naive Rats", C.A., v. 99, 100796b.
Ebenezer, "Atropine Pretreatment Interferes with the Development of Tolerance to the Depressant Effect of Nicotine", C.A., v. 99, 100797c.
Jaffe, "Tobacco Use and Tobacco Use Disorder", Psychopharmacology: A Generation of Progress, pp. 1665–1676, Raven Press, (1978).

*Primary Examiner*—Stanley J. Friedman
*Attorney, Agent, or Firm*—Pravel, Gambrell, Hewitt & Kimball

[57] ABSTRACT

Subcutaneously injecting a patient with a solution of atropine and scopolamine, potentiated by chlorpromazine alleviates withdrawal symptoms attributed to the cessation of chronic nicotine blockage. Auricular injections give immediate effects and minimize peripheral anti-cholinergic activity. The treatment is administered during an initial office visit.

5 Claims, No Drawings

METHOD FOR ANTI-CHOLINERGIC BLOCKAGE OF WITHDRAWAL SYMPTOMS IN SMOKING CESSATION

BACKGROUND OF THE INVENTION

Since the introduction of tobacco into the civilized world by Columbus' sailors returning from the Americas, nicotine has become the most widespread form of substance dependency in the world. It is legal, encouraged with advertising, and used in any human setting, although it causes more morbidity and mortality than all other drugs combined. Recidivism in individuals who attempt to quit smoking—75%—equals that of recidivism of heroin addicts.

A variety of methods to stop smoking addiction have been tried including hypnotism, psychotherapy, electro-shock aversion, and group counseling. A recent assessment of the success of smoking programs and clinics shows that fewer than half of the smokers participating in such programs quit and less than 25%–30% remain non-smokers 9–18 months later. Evan Richard I., Henderson Allen H., Hill Peter C. and Raines, Betteye: Current Psychological, Social, and Educational Programs in Control and Prevention of Smoking; a Critical Methodological Review. Atherosclerosis Reviews, 1979; 6:201–241.

It is well documented that nicotine has an agonistic action at nicotine receptor sites in the parasympathetic nervous system. Its primary action upon prolonged use is that of a blocking agent. While this activity is less documented in the central rather than the peripheral nervous system, the preponderance of such nicotine receptors appears to be located at the mid-brain level.

With chronic nicotine use, biochemical tolerance and dependency are developed at specific parasympathetic neuro-receptor sites by increased acetylcholine accumulation mediated via enzyme induction and/or de-repression through choline acetyltransferase.

Mammalian studies on the superior cervical ganglia show that chronic nicotine treatment causes acetylcholine increase of about 35%. Marked neuro-transmitter changes occur after withdrawal of nicotine resulting in the reduction of acetylcholine accumulation even to sub-normal levels, normalization of the choline acetyltransferase, and an increase of acetylcholinesterase to about 117% of controls. This activity results from the cessation of nicotine stimulation and an increased release of acetylcholine from nerve axons.

A "tobacco withdrawal syndrome" to nicotine abstinence thus comes about by elimination of the nicotine blockage at specific nicotine-cholinergic synapses. Tolerance and dependency developed by increased acetylcholine synthesis are now replaced by withdrawal, which is brought about by excessive acetylcholine stimulation. The final biochemical interpretation of nicotine withdrawal—i.e., excessive acetylcholine rebound bombardment of lower mid-brain nicotine receptor sites—is through acetylcholine inter-synaptic stimulation of predominently muscarinic cholinergic sites at higher neuronal levels, including the cerebral cortex. Physical effects of cessation of tobacco smoking manifest themselves as a decrease in heart rate and blood pressure, increased irritability, nervousness, gastrointestinal disturbances, EEG changes and lack of concentration. Similar effects exist through excessive acetylcholine stimulation mediated by di-isoflurophosphate (DFP) poisoning in humans.

In response to tobacco withdrawal symptoms, the dependent smoker resumes his nicotine titration for immediate relief and returns to his prior state of "normality." Glick, Jarvick and Nakamura tested a variety of anti-cholinergic and other drugs and found that only scopolamine and d-amphetamine decreased smoking (puffing pattern) in monkeys. Glick SD, Jarvick ME, and Nakamura NK, Inhibition by Drugs of Smoking Behavior in Monkeys, Nature, Aug. 29, 1970; 227: 969–71.

SUMMARY OF THE INVENTION

By subcutaneously injecting a patient with a solution of atropine, and scopolamine, potentiated by chlorpromazine, the immediate effects of excessive acetylcholine stimulation at cerebro-cortical sites caused by inter-synaptic rebound from lower, nicotine mid-brain receptors is inhibited. This alleviates withdrawal symptoms attributed to the cessation of chronic nicotine blockage. Auricular injections give immediate effects and minimize peripheral anti-cholinergic activity. The treatment is administered during an initial office visit.

Chlorpromazine in solution potentiates the antidotal effectiveness of atropine, providing a protection ratio of 10 compared to the use of atropine with a variety of other central nervous system depressant drugs, such as sedatives, neuroleptics and anti-convulsants. The anti-cholinergic drugs act predominently at muscarinic sites in the cerebral cortex; these sites ultimately interpret the inter-synaptic rebound phenomenon caused by excessive acetylcholine stimulation at lower nicotine midbrain level receptors created by cessation of chronic nicotine use.

Following the initial office visit and treatment, the patient may be placed upon oral doses of predominently centrally acting anti-cholinergic drugs for a period of up to two weeks or longer, as clinically indicated.

DESCRIPTION OF THE PREFERRED EMBODIMENTS

Preliminary to receiving treatment by the anti-cholinergic block method, a patient admitted for treatment answers a smoking questionnaire and completes a medical history with particular attention paid to acute angle glaucoma, prostatic-hypertrophy, cardiac arrhythmias or bladder dysfunction. Surgical history is also recorded, noting any idiosyncratic or prolonged refractory times in the decay of anti-cholinergic drugs. A routine examination is performed consisting of a chest X-ray, EKG, urinalysis, complete blood count, serum-electrolytes and SMA-12 panel. Patients not treated by the method are those with the usual medical contraindications to anti-cholinergic drugs.

Patients which appear from the preliminary examination to be suitable candidates for treatment by the anti-cholinergic block method are further checked for possible adverse reaction to the method by injection of an intramuscular dose of a solution containing 0.1 mg scopolamine, 0.3 mg atropine and 15.0 mg chlorpromazine. Thereafter, pupillary reflex is examined after 5 minutes in a darkened room. Patients who have normal pupillary constriction and offer no complaint of excessive xerostomia are suitable candidates for treatment in accordance with the anti-cholinergic block method.

In accordance with the anti-cholinergic block method, suitable candidate patients are given one or more injections of specific acetylcholine antagonists which block the cerebral sites and stop both the patient's physical craving for nicotine and the withdrawal symptoms. The solution with which patients are injected comprises a carrier or diluent containing atropine, scopolamine and, as a potentiator, chlorpromazine. The carrier or diluent may be pure water, a normal saline solution, an aqueous solution containing procaine, a or any other diluent commonly employed as a carrier for pharmaceutical compounds administered by injection. Preferably, a procaine diluent is used, such as two percent (2%) procaine in water, since procaine is a local anesthetic which facilitates patient comfort upon administration of the injection at the preferred injection site, behind the ear. The compounds incorporated into the injectable solution as acetylcholine antagonists are atropine and scopolamine. Chlorpromazine is incorporated into the solution as a potentiator for atropine and scopolamine. The solution is prepared in concentrations to contain a unit dosage of from about 0.1 to about 0.8 mg atropine, from about 0.2 to about 0.4 mg scopolamine, and from about 10 to about 50 mg chloropromazine. Preferably, a unit dosage of the solution is prepared containing 0.1 mg atropine, 0.3 mg scopolamine and 10 mg chlorpromazine. The precise composition of the solution may be tailored to the requirements of an individual patient. For patients who, upon prior attempts to cease smoking, have experienced indicate a feeling of greater than normal irritability, nervousness, lack of concentration or gastro-intestinal disturbances, the amounts of atropine and chlorpromazine in the solution may be increased to provide greater blocking affinity at the cerebral sites; hence, more effective relief against the craving for nicotine. However, in the typical case, a solution containing unit dosages of 0.1 mg atropine, 0.3 mg scopolamine and 10 mg chlorpromazine has been found to be effective and to give good results.

Preferably, the patient is treated by injecting a solution containing 0.1 mg atropine with 0.3 mg scopolamine and 10.0 mg chlorpromazine with one-half the dosage administered subcutaneously behind each ear. This site is utilized behind the pinnae because the tributory veins in the auricular area contain no valves, thus permitting a rapid onset of anti-cholinergic activity directed primarily toward the central nervous system. Alternatively, the site for injection may be into the conchae, although for purposes of minimum patient discomfort, injection behind the ear is preferred. The volume of solution for injection, as a total, may range from about 0.4 cc to about 1.2 cc, preferably with half of such volume administered behind each ear. For purposes of patient comfort, it is preferred that the volume of solution administered at each ear not exceed 0.4 cc. Treatment in accordance with this method alleviates the physical symptoms of the nicotine withdrawal syndrome to which a patient would otherwise be subjected due to the build-up of excessive acetycholine upon cessation of smoking.

Typically, following treatment the patient experiences xerostomia, some lightheadedness and difficulty focusing. These effects dissipate in 6 to 8 hours; patient complaints of altered taste and smell, however persist for approximately 24 hours. Treated patients are cautioned to drink no alcohol and to avoid driving for 24 hours. They are instructed not to take any medication with a synergistic effect. Patients experienced in physiologic withdrawal to smoking cessation quickly note the absence of smoking withdrawal symptoms upon treatment.

As a follow-up to treatment by the anti-cholinergic block method, a variety of medications may then be prescribed for the subsequent two-week period. Anticholinergic drugs such as trihexyphenidyl hydrochloride, benztropine mesylate or scopolamine patches may be taken by the patient on a prescribed basis. These particular anti-cholinergic medications are prescribed because of their predominately central, rather than peripheral, parasympathetic blocking activity.

Since withdrawal symptoms to nicotine cessation are most pronounced during the first 24–48 hours, immediate and high levels of anti-cholinergic activity are achieved by subcutaneously injecting the described anti-cholinergic drugs behind the auricular areas. Nicotine is eliminated in approximately three days, but the reduction in the withdrawal symptoms may require a period of approximately two weeks. As a consequence, oral medication is recommended to maintain a low level of anti-cholinergic activity for a period of up to two weeks. This technique is based on laboratory evidence that approximately two weeks are required for significant decrease in enzyme synthesis of the end product (acetylcholine). The anti-cholinergic method helps patients develop an aversion to cigarettes by also affecting taste and sensory receptors. The effect of dry mouth, for example, while disadvantageous in many instances, is helpful where it is a consequence of therapeutic techniques.

Patients who wanted to stop their smoking dependency were clinically treated with injections of various specific acetylcholine antagonists. Smokers were referred by other physicians and also enrolled in response to stop-smoking advertisements. Smokers were grouped according to age, sex, quantity of cigarettes smoked, years of continuous smoking, nicotine content of cigarettes, and verbalization of a Specific Motivational Reason (SMR) for quitting. Menthol versus non-mentholated tobacco users were also evaluated. During the initial period of the clinical study, patients were treated with a procaine solution containing atropine and scopolamine. Some patients were treated with solutions to which mecalamine and other competitive inhibitors were added. In the later stages of the study, the composition of the treating solution was changed to that previously described, namely, atropine and scopolamine as potentiated by addition of chlorpromazine.

During the course of the clinical study, a sampling of 500 patients were treated by auricular injection of a solution containing atropine and scopolamine in unit dosages of 0.1 mg and 0.3 mg, respectively. This sampling of patients was evaluated at two months and twelve months following treatment to determine the percentage of the patient population which remained non-smokers. Likewise, a second sampling of patients was treated by auricular injection of a solution containing atropine, scopolamine and chlorpromazine in unit dosages of 0.1 mg, 0.3 mg and 10.0 mg, respectively. Again, the patient population treated with solutions containing chlorpromazine was evaluated at two and twelve months following treatment to determine the percentage of the patient population which remained non-smokers.

As of the two month follow up evaluation, it was found that of the 500 patient population treated with solutions not containing chlorpromazine 66.2 percent had remained non-smokers, whereas of the 500 patient population treated with solutions containing chlorpromazine 86.8 percent of the population had remained non-smokers for two months following treatment. As of the twelve month follow up evaluation, the population of patients treated with chlorpromazine containing solutions consisted of 100 patients. To compare the efficacy of treatment with and without chlorpromazine as a component of the solution, a random sampling of 100 patients from the population treated with solutions not containing chlorpromazine was selected for comparison purposes. At twelve months following treatment, 39.8 percent of the patient population treated with chlorpromazine containing solutions continued to remain as non-smokers, whereas only 19.1 percent of the sample population of patients treated with solutions not containing chlorpromazine remained non-smokers after twelve months.

The random patient sampling of 100 patients involved in the initial treatment regimen (with no chlorpromazine) indicates that, at twelve months, there is a statistically significant difference in recidivism between that test group and the later patient population which was treated with the chlorpromazine containing solutions. Those treated with solutions of atropine and scopolamine potentiated by chlorpromazine had a success rate for abstaining from smoking more than double that of patients treated with atropine and scopolamine solutions not containing chlorpromazine.

I claim:

1. A method for conditioning a patient to minimize physical withdrawal symptoms associated with cessation of chronic tobacco smoking by the patient, comprising:

injecting subcutaneously into an auricular area of said patient from about 0.4 to about 1.2 cc of a solution containing a unit dosage of from about 0.1 to about 0.8 mg atropine, from about 0.2 to about 0.4 mg scopolamine, and from about 10.0 to about 50.0 mg chlorpromazine in a suitable carrier.

2. The method of claim 1, wherein the carrier is an aqueous solution containing procaine.

3. The method of claim 1, wherein the solution contains as a unit dosage 0.1 mg atropine, 0.3 mg scopolamine and 10.0 mg chlorpromazine.

4. The method of claim 3, wherein one-half of the solution dosage is injected subcutaneously behind each ear.

5. The method of claim 3, wherein one-half of the solution dosage is injected subcutaneously into the conchae of said patient.

* * * * *